United States Patent [19]
Heitsch et al.

[11] Patent Number: 5,786,365
[45] Date of Patent: Jul. 28, 1998

[54] USE OF NONPEPTIDE BRADYKININ ANTAGONISTS FOR THE TREATMENT AND PREVENTION OF CHRONIC FIBROGENETIC LIVER DISORDERS, ACUTE LIVER DISORDERS AND THE COMPLICATIONS ASSOCIATED THEREWITH

[75] Inventors: Holger Heitsch, Mainz-Kastel; Adalbert Wagner, Gersthofen; Klaus Wirth, Kriftel; Max Hropot, Flörsheim; Martin Bickel, Bad Homburg, all of Germany

[73] Assignee: Hoechst Aktiengesellschaft, Frankfurt am Main, Germany

[21] Appl. No.: 858,550

[22] Filed: May 19, 1997

[51] Int. Cl.$^6$ ...................... A61K 31/47
[52] U.S. Cl. .............. 514/311; 514/312; 514/313; 514/314
[58] Field of Search ............... 514/311, 312, 514/313, 314

[56] References Cited

U.S. PATENT DOCUMENTS

| | | |
|---|---|---|
| 5,212,182 | 5/1993 | Musser et al. |
| 5,216,165 | 6/1993 | Mobilio et al. |
| 5,438,064 | 8/1995 | Mobilio et al. |

FOREIGN PATENT DOCUMENTS

| | | |
|---|---|---|
| 0 622 361 A1 | 11/1994 | European Pat. Off. |
| 0662361 | 11/1994 | European Pat. Off. |
| 9604251 | 3/1995 | WIPO |
| 0 774 462 A1 | 2/1996 | WIPO |

OTHER PUBLICATIONS

Brockmann et al., Chem. Ber., vol. 103:708–717 (1970).
König et al., Chem. Ber., vol. 103:2052–2061 (1970).
Schrier et al., Peripheral Arterial Vasodilation Hypothesis: a Proposal for the Initiation of Renal Sodium and Water Retention in Cirrhosis, vol. 8 (5):1151–1157 (1988).
Madeddu et al., Effects of Hoe, 140, a bradykinin $B_2$-receptor antagonist, on renal function in conscious normotensive rats, Br. J. Pharmacol., vol. 106:380–386 (1992).
Majima et al., High Sensitivity to Salt in Kininogen–Deficient Brown Norway Katholiek Rats, Hypertension, vol. 22 (5):705–714 (1993).

*Primary Examiner*—James H. Reamer
*Attorney, Agent, or Firm*—Finnegan, Henderson, Farabow, Garrett & Dunner, L.L.P.

[57] ABSTRACT

The invention relates to the use of nonpeptide bradykinin antagonists for the production of pharmaceuticals for the treatment of chronic fibrogenetic liver disorders (hepatic cirrhosis and hepatic fibrosis), acute liver disorders and for the prevention of complications, in particular for the prophylaxis or treatment of portal hypertension, decompensation symptoms such as ascites, edema formation, hepatorenal syndrome, hypertensive gastropathy and colopathy, splenomegaly and hemorrhagic complications in the gastrointestinal tract due to portal hypertension, collateral circulation and hyperemia and a cardiopathy as a result of a chronically hyperdynamic circulatory situation and its consequences.

4 Claims, No Drawings

USE OF NONPEPTIDE BRADYKININ ANTAGONISTS FOR THE TREATMENT AND PREVENTION OF CHRONIC FIBROGENETIC LIVER DISORDERS, ACUTE LIVER DISORDERS AND THE COMPLICATIONS ASSOCIATED THEREWITH

BACKGROUND OF THE INVENTION

Bradykinin and related peptides are potent vasoactive, endogenous substances which produce inflammation and pain. EP-A 622 361, U.S. Pat. No. 5,212,182, U.S. Pat. No. 5,216,165, U.S. Pat. No. 5,438,064, WO 9604251 and unpublished German Patent Application No. 19610784.9 disclose substituted, fused heterobicycles and their use as bradykinin receptor antagonists and their use as agents for the control of conditions which are mediated, induced or supported by bradykinin.

Surprisingly, it has now been found that nonpeptide bradykinin antagonists of this structural type are moreover suitable agents for the treatment of chronic fibrogenetic liver disorders (hepatic cirrhosis and hepatic fibrosis) and acute liver disorders and for the prevention of complications, in particular for the prophylaxis or treatment of portal hypertension, decompensation symptoms such as ascites, edema formation, hepatorenal syndrome, hypertensive gastropathy and colopathy, splenomegaly and hemorrhagic complications in the gastrointestinal tract due to portal hypertension, collateral circulation and hyperemia and a cardiopathy as a result of a chronically hyperdynamic circulatory situation and its consequences.

SUMMARY OF THE INVENTION

Suitable compounds are nonpeptide bradykinin antagonists which show a natriuretic and diuretic effect in the model of $CCl_4$-induced hepatic fibrosis in the rat.

Suitable nonpeptide bradykinin antagonists are, inter alia, the compounds of the formula (I)

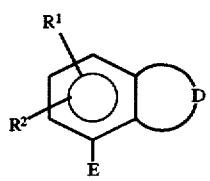

(I)

in which the symbols have the following meaning:

D is
1. a radical of the formula (II):

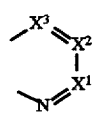

(II)

2. a radical of the formulae (III) to (VI):

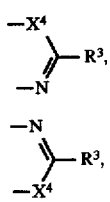

(III)

(IV)

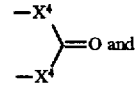

(V)

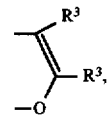

(VI)

E is
1. a radical of the formula (VII):

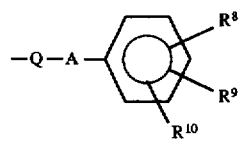

(VII)

2. hydrogen, halogen, $(C_1-C_4)$-alkyl, $(C_1-C_4)$-alkylthio, $(C_1-C_4)$-alkoxy, where in the last 3 radicals 1 or more hydrogen atoms can be replaced by fluorine;

$X^1$ is nitrogen or C—$R^4$;
$X^2$ is nitrogen or C—$R^5$;
$X^3$ is nitrogen or C—$R^6$;
$X^4$ is oxygen, nitrogen or N—$R^7$;
$R^1, R^2$ are identical or different and are hydrogen, halogen, $(C_1-C_4)$-alkyl or $(C_1-C_4)$-alkoxy;
$R^3$ is hydrogen, halogen, $(C_1-C_6)$-alkyl, $(C_6-C_{12})$-aryl, $(C_1-C_3)$-alkyl-$(C_6-C_{12})$-aryl, $(C_3-C_5)$-alkenyl, $(C_1-C_4)$-alkoxy, $CO_2R^{11}$;
$R^4$ is hydrogen, halogen, $(C_1-C_4)$-alkyl, hydroxyl, $(C_1-C_4)$-alkylthio, amino, $(C_1-C_4)$-alkylamino, $(C_1-C_4)$-dialkylamino, $(C_1-C_4)$-alkoxy, which is optionally substituted by hydroxyl, $(C_1-C_4)$-alkoxy, amino or $(C_1-C_4)$-alkylamino, and $(C_6-C_{12})$-aryl, optionally substituted by $(C_1-C_4)$-alkyl or $CO_2R^{11}$;

$R^5$ is
1. hydrogen or $(C_1-C_4)$-alkyl

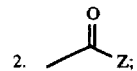

$R^6$ is
1. hydrogen, halogen, $(C_1-C_4)$-alkyl, hydroxyl, $(C_1-C_4)$-alkylthio, amino, $(C_1-C_4)$-alkylamino, $(C_1-C_4)$-dialkylamino, $(C_1-C_4)$-alkoxy, which is optionally substituted by hydroxyl, $(C_1-C_4)$-alkoxy, amino or $(C_1-C_4)$-alkylamino, and $(C_6-C_{12})$-aryl, optionally substituted by $(C_1-C_4)$-alkyl or $CO_2R^{11}$;
2. a radical of the formula (VIII):

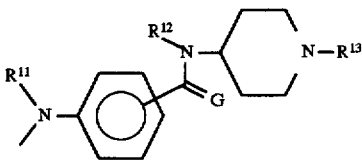

(VIII)

$R^7$ is $(C_1-C_4)$-alkyl, $(C_6-C_{12})$-aryl, or $(C_1-C_3)$-alkyl-$(C_6-C_{12})$-aryl;
$R^8, R^9$ are identical or different and are hydrogen or halogen;
A is $(C_1-C_3)$-alkanediyl;
Q is O or $NR^{11}$;

$R^{10}$ is a radical of the formula (IX)

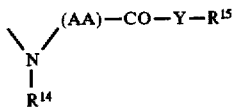

$R^{11}$, $R^{14}$ are hydrogen or $(C_1-C_4)$-alkyl;
G is or $H_2$;
$R^{12}$ is hydrogen if G=O and hydrogen or $R^{16}CO$ if G=$H_2$;
$R^{13}$ is $(C_1-C_4)$-alkyl, $(C_3-C_7)$-cycloalkyl, —$(CH_2)_m$—$(C_3-C_7)$-cycloalkyl, —$(CH_2)_m$—$CONR^{11}R^{11}$, or

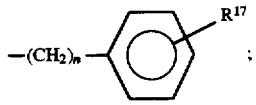

m, n are identically or differently a number 0–6;
AA is an amino acid comprising, methionine, alanine, phenylalanine, 2-chlorophenylalanine, 3-chlorophenylalanine, 4-chlorophenylalanine, 2-fluorophenylalanine, 3-fluorophenylalanine, 4-fluorophenylalanine, tyrosine, o-methyltyrosine, β-(2-thienyl)-alanine, glycine, cyclohexylalanine, leucine, isoleucine, valine, norleucine, phenylglycine, serine, cysteine, aminopropionic acid or aminobutyric acid;
Y is
1. $(C_2-C_6)$-alkenediyl,
2. $(C_1-C_8)$-alkanediyl,
3. $(C_3-C_{10})$-cycloalkenediyl,
4. —$(CH)_p$—$T_o$—$(CH_2)_q$—, where 1. to 4. can optionally be substituted by one or more radicals such as, for example, O—$R^{18}$, $NO_2$, CN, $CO_2R^{11}$, $SO_3R^{18}$, $NR^{20}R^{21}$, $SO_2NR^{20}R^{21}$, $CONR^{20}R^{21}$;
T is O, $NR^{21}$ or S;
o is a number 0 or 1;
p,q are identical or different and are a number from 0 to 6;
$R^{15}$ is
1. hydrogen,
2. $(C_1-C_5)$-alkyl,
3. $(C_6-C_{10})$-aryl,
4. $(C_1-C_9)$-heteroaryl, where 3. and 4. can optionally be substituted by one or more groups, such as halogen, CN, $NO_2$, $(C_1-C_6)$-alkyl, $(C_6-C_{10})$-aryl, $(C_2-C_5)$-alkenyl, where the last three radicals can optionally be partially or completely substituted by halogen, $(C_1-C_5)$-alkoxy; $(C_1-C_5)$-alkylthio, $NR^{20}R^{21}$, $CO_2R^{19}$, $SO_3R^{18}$, $SO_2NR^{20}R^{21}$, $SO_2R^{18}$, O—$R^{18}$; $NR^{20}CO$—$R^{15}$;
$R^{16}$ is hydrogen, $(C_1-C_4)$-alkyl, $(C_6-C_{12})$-aryl, $(C_1-C_4)$-alkyl-$(C_6-C_{12})$-aryl, perfluoro-$(C_1-C_4)$-alkyl;
$R^{17}$ is hydrogen, halogen, $(C_1-C_4)$-alkyl, $(C_1-C_4)$-alkoxy, perfluoro-$(C_1-C_4)$-alkyl, $NO_2$, OH, $NH_2$, $CONR^{16}R^{16}$, $NR^{16}CONR^{16}R^{16}$;
$R^{18}$, $R^{19}$, $R^{20}$ are identical or different and are hydrogen, $(C_1-C_5)$-alkyl, $(C_3-C_5)$-alkenyl, $(C_6-C_{12})$-aryl-$(C_1-C_3)$-alkyl, $(C_3-C_{10})$-cycloalkyl, $(C_3-C_{10})$-cycloalkyl-$(C_1-C_3)$-alkyl, C(O)—O—$(C_1-C_5)$-alkyl, or C(O)—NH—$(C_1-C_5)$-alkyl;
$R^{21}$ is hydrogen, C(O)—O—$(C_1-C_5)$-alkyl, C(O)—O—$(C_1-C_3)$-alkyl-$(C_6-C_{10})$-aryl;
Z is —$R^{14}N$—$R^{22}$;

$R^{22}$ is

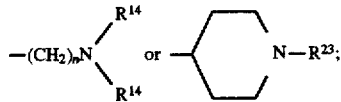

$R^{23}$ is $(C_1-C_4)$-alkyl,

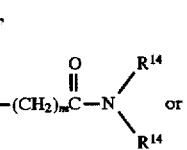

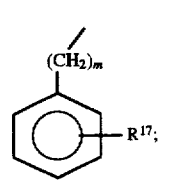

and their physiologically tolerable salts.

DETAILED DESCRIPTION OF THE INVENTION

The disclosure of German Patent Application Nos. 19620509.3 filed May 22, 1996, 19632042.9, filed Aug. 8, 1996, 19639303.5, filed Sep. 25, 1996 and 19610784.9 filed Mar. 19, 1996 are hereby incorporated by reference.

Alkyl and alkenyl can be straight-chain or branched. The same applies to radicals derived therefrom such as, for example, alkoxy.

Alkenyl is mono- or polyunsaturated compounds such as, for example, 1,4-butadienyl, 8,11-heptadienyl, 8,11,14-heptatrienyl, butenyl. The same applies to cycloalkenyl. Cycloalkyl is mono- or bicyclic compounds such as, for example, cyclopropyl, cyclopentyl, cyclohexyl, bicyclononyl. The same applies to cycloalkenyl.

$(C_6-C_{12})$-Aryl is, for example, phenyl, naphthyl or biphenylyl, preferably phenyl. The same applies to radicals derived therefrom, such as, for example, aralkyl.

Halogen (Hal) is fluorine, chlorine, bromine or iodine, preferably chlorine or fluorine.

$(C_1-C_9)$-Heteroaryl is understood as meaning radicals which are derived from phenyl or naphthyl, in which one or more CH groups are replaced by N and/or in which at least two adjacent CH groups are replaced (with formation of a five-membered aromatic ring) by S, NH or O. In addition, one or both atoms of the condensation site of bicyclic radicals (such as in indolizinyl) can also be nitrogen atoms.

Heteroaryl is counted in particular as furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl, cinnolinyl, benzopyranonyl, coumarinyl, pyranonyl, furandionyl.

Physiologically tolerable salts of compounds of the formula (I) are understood as meaning both their organic and inorganic salts, as are described in Remington's Pharmaceutical Sciences (A. R. Gennard Editior, Mack Publishing Co., Easton Pa., 17th Edition, page 1418 (1985)). On account of the physiological and chemical stability and of the solubility, acidic groups are preferred, inter alia sodium, potassium, calcium and ammonium salts; for basic groups, inter alia, salts of hydrochloric acid, sulfuric acid, phosphoric acid or of carboxylic acids or sulfonic acids, such as, for example acetic acid, citric acid, benzoic acid, maleic acid, fumaric acid, tartaric acid and p-toluenesulfonic acid are preferred.

Suitable nonpeptide bradykinin antagonists and their preparation are, for example, described in the Patent Applications EP-A 622 361, WO 9604251, German Application No.19610784.9 and U.S. Pat. Nos. 5,212,182, 5,216,165 and 5,438,064, the disclosures of which are hereby incorporated by reference, in which compounds of formula IA,

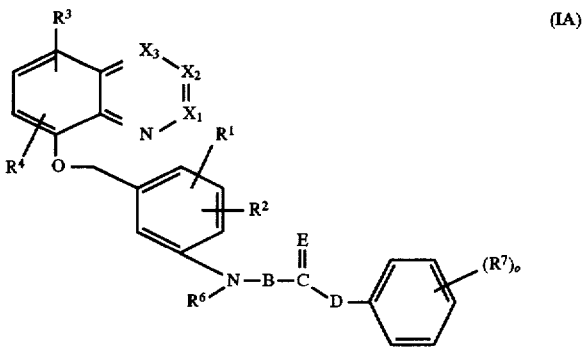

are disclosed, wherein the symbols have the following meaning:

a) $X_1$–$X_3$, identically or differently, are N or $CR^5$;
b) $R^1$ and $R^2$, identically or differently, are
 (1) H
 (2) halogen;
c) $R^3$ and $R^4$, identically or differently, are
 (1) H
 (2) halogen
 (3) ($C_1$–$C_5$)-alkyl
 (4) ($C_2$–$C_5$)-alkenyl;
d) $R^5$ is
 (1) H
 (2) halogen
 (3) ($C_1$–$C_6$)-alkyl
 (4) O—$R^6$
 (5) S—$R^6$
 (6) $NHR^6$
 (7) ($C_6$–$C_{12}$)-aryl
 (8) ($C_6$–$C_{12}$)-aryl-($C_1$–$C_3$)-alkyl
 (9) —C(O)—$OR^6$
 (10) —C(O)—H;
where (3), (7) and (8) can optionally be substituted by one or more groups such as, for example, $OR^6$, $SR^6$, $NO_2$, CN, $NHR^6$ or halogen
e) $R^6$ and $R^8$, identically or differently, are
 (1) H
 (2) ($C_1$–$C_5$)-alkyl
 (3) ($C_3$–$C_5$)-alkenyl
 (4) ($C_6$–$C_{12}$)-aryl-($C_1$–$C_3$)-alkyl;
f) $R^7$ is
 (1) ($C_1$–$C_5$)-alkyl, where hydrogen is partially or completely replaced by fluorine or chlorine
 (2) ($C_1$–$C_5$)-alkoxy, where hydrogen is partially or completely replaced by fluorine or chlorine;
g) B is an aminocarboxylic acid, e.g. methionine, alanine, phenylalanine, 2-chlorophenylalanine, 3-chlorophenylalanine, 4-chlorophenylalanine, 2-fluorophenylalanine, 3-fluorophenylalanine, 4-fluorophenylalanine, tyrosine, O-methyltyrosine, β-(2-thienyl)alanine, glycine, cyclohexylalanine, leucine, isoleucine, valine, norleucine or phenylglycine, serine or cysteine, aminopropionic acid, aminobutyric acid;
h) D is
 (1) ($C_2$–$C_5$)-alkenediyl
 (2) ($C_1$–$C_5$)-alkanediyl
 (3) —$(CH_2)_n$—$Y_p$—$(CH_2)_m$—;
i) E is
 (1) O
 (2) S;
j) Y is
 (1) O
 (2) S
 (3) $NR^8$;
k) n and m, identically or differently, are a number 0–3;
l) o is a number 1–3;
m) p is a number 0 or 1;

and their physiologically tolerable salts. The preparation of compounds of the formula (IA) is achieved by a process, which comprises a) deprotonating a compound of the formula (XII),

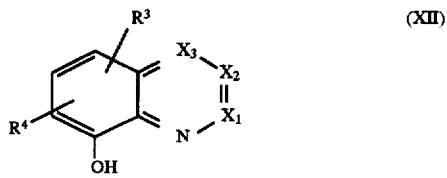

in which $X_1$–$X_3$ and $R^3$ and $R^4$ are as defined in formula (IA) above, using $CS_2CO_3$ or $K_2CO_3$ in an inert solvent, preferably DMF or N-methylpyrrolidine, and reacting it at room temperature with a compound of the formula (XIII)

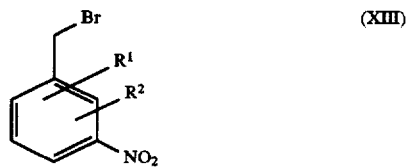

in which $R^1$ and $R^2$ are as defined in formula (IA) above;

b) reducing the compound thus obtained of the formula (XIV)

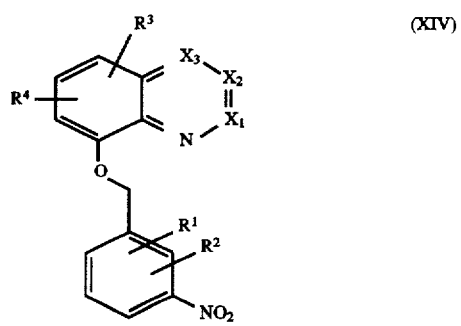

in which $R^1$, $R^2$, $R^3$, $R^4$, $X_1$, $X_2$ and $X_3$ are as defined in formula (IA) above, with the aid of transition metal halides, preferably $SnCl_2$ or $FeCl_3$, to give a compound of the formula (XV)

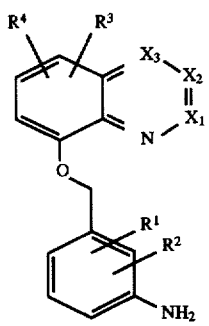

in which $R^1$, $R^2$, $R^3$, $R^4$, $X_1$, $X_2$ and $X_3$ are as defined in formula (IA) above;

c) reacting a compound of the formula (XV) with activated, suitably protected aminocarboxylic acid derivatives of B (B-Prot), preferably the acid chlorides of the phthaloyl-protected aminocarboxylic acid derivatives of B, in inert solvents such as, for example, NMP, if appropriate by addition of DMAP, and thus obtaining a compound of the formula (XVI)

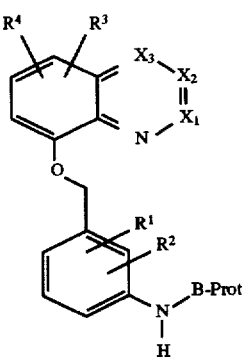

in which B, $R^1$, $R^2$, $R^3$, $R^4$, $X_1$, $X_2$ and $X_3$ are as defined in formula (IA) above, and Prot is an amino protective group, such as described in T. W. Greene "Protective Groups in organic Synthesis", John Wiley, 2nd Edition, 1991, e.g. phthaloyl, benzyl or paramethoxybenzyl;

d) reacting a compound of the formula (XVI), after action of alkali metal hydrides, alkali metal carbonates or alkoxides in inert solvents, preferably DMF or NMP, has taken place, followed by a treatment with $R^6X$, where $R^6$ is as defined in formula (IA) above and X is a leaving group, e.g. halogen, mesylate or tosylate, a compound of the formula (XVII) being obtained

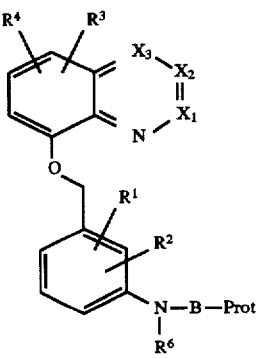

in which B, $R^1$, $R^2$, $R^3$, $R^4$, $R^6$, $X_1$, $X_2$ and $X_3$ are as defined in formula (IA) above and Prot is as defined in formula (XVI) above;

e) to remove the protective group (Prot) from the compound of the formula (XVII), in the case of the phthaloyl group preferably reacting with hydrazine in alcohols as solvents at temperatures between room temperature and the boiling point, preferably at room temperature, a compound of the formula (XVIII) being obtained

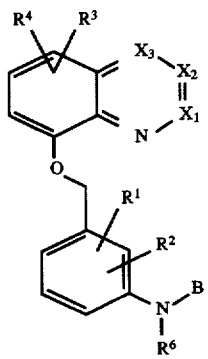

in which B, $R^1$, $R^2$, $R^3$, $R^4$, $R^6$, $X_1$, $X_2$ and $X_3$ are as defined in formula (IA) above and Prot is as defined in formula (XVI) above;

$f_1$) reacting a compound of the formula (XVIII) with activated carboxylic acid derivatives of the formula (XIX)

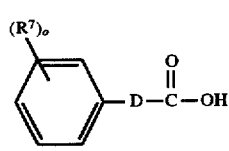

in which $R^7$, o and D are as defined in formula (IA) above, preferably their acid chlorides or carboxylic acids of the formula (XIX), activated by reagents such as are used in peptide synthesis, or $f_2$) reacting a compound of the formula (XVIII) with an amine or an alcohol of the formula (XX)

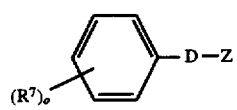

in which $R^7$, o and D are as defined above and Z is OH or $NH_2$, the compound of the formula (XVIII) or (XX), however, first being reacted with a doubly activated carbonyl compound to form the urea or urethane group, e.g. with carbodiimides, phosgene or chlorocarbonic acid esters, preferably phosgene and carbonyidiimidazole, preferably at temperatures between 0° C. and room temperature in inert solvents, preferably dichloromethane or dimethoxyethane, or $f_3$) reacting a compound of the formula (XVIII) with an appropriate isocyanate or isothiocyanate, preferably at temperatures between 0° C. and room temperature in inert solvents, preferably dichloromethane or dimethoxyethane, and g) if appropriate, converting the compound of the formula (IA) obtained into its physiologically tolerable salts by known methods.

Conversion to the bromomethyl compound is carried out by reaction of the corresponding methyl derivative with N-bromosuccinimide, dibromohydantoin or bromine in inert solvents, preferably bromobenzene or cyclohexane at temperatures from 60° C. up to the boiling point.

The coupling reagent used can be all possible activating reagents used in peptide synthesis, see, for example, Houben-Weyl, Methoden der Organischen Chemie, [Methods of Organic Chemistry], volume 15/2, Georg Thieme Verlag, Stuttgart 1974, but in particular carbodiimides such as, for example, N,N'-dicyclohexylcarbodiimide, N,N'-diisopropyl-carbodiimide or N-ethyl-N'-(3-dimethylaminopropyl)carbodiimide. Coupling can be carried out in this case directly by addition of carboxylic acid derivative to the activating reagent and, if appropriate, an additive such as, for example, 1-hydroxybenzotriazole (HOBt) (W. König, R. Geiger, Chem. Ber. 103, 708 (1970)) or 3-hydroxy-4-oxo-3,4-dihydrobenzotriazine (HOObt) (W. König, R. Geiger, Chem. Ber. 103, 2054 (1970)) or else the preactivation of the carboxylic acid derivative as a symmetrical anhydride or HOBt or HOObt ester can be carried out separately and the solution of the activated species in a suitable solvent can be added to the amine.

The coupling or activation of the amino acid derivatives to one of the above-mentioned activating reagents can be carried out in dimethylformamide, N-methylpyrrolidone or methylenechloride or a mixture of the solvents mentioned.

Instead of the phthaloyl group, protective groups can also be used which protect both protons of the amino group, e.g. 2 benzyl groups.

Particularly suitable compounds of the formula I are those in which:

D is a radical of the formula (X)

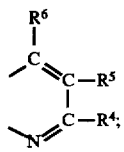
(X)

E is 1. a radical of the formula (XI)

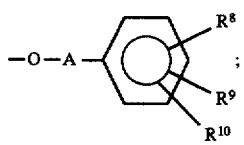
(XI)

2. hydrogen, $(C_1-C_4)$-alkyl or $(C_1-C_4)$-alkoxy;

$R^1,R^2$ are identical or different and are hydrogen, halogen or $(C_1-C_4)$-alkyl;

$R^4$ is hydrogen, $(C_1-C_4)$-alkyl, phenyl or methoxy;

$R^5$ is 1. hydrogen or $(C_1-C_4)$-alkyl;

2. 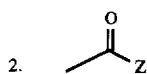

$R^6$ is 1. hydrogen or $(C_1-C_4)$-alkyl 2. a radical of the formula (VIII):

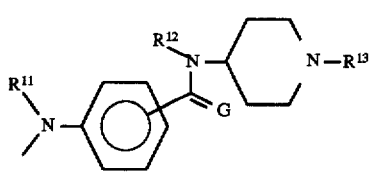
(VIII)

$R^8,R^9$ are identical or different and are hydrogen or chlorine;
A is —$CH_2$— or —$CH_2$—$CH_2$—;

$R^{10}$ is a radical of the formula (IX):

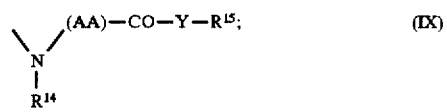
(IX)

$R^{11},R^{14}$ are hydrogen, methyl or ethyl;
G is O or $H_2$;
$R^{12}$ is hydrogen if G is equal to O or hydrogen or $R^{16}CO$ if G is equal to $H_2$;
$R^{13}$ is $(C_1-C_4)$-alkyl, cyclopentyl, cyclohexyl, —$(CH_2)_m CONR^{11}R^{11}$,

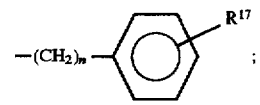

m,n are identically or differently a number 0–2;
AA is the amino acid glycine or alanine;
Y is 1. $(C_2-C_5)$-alkenediyl,
2. $(C_2-C_4)$-alkanediyl,
3. —$(CH_2)_p$—$T_o$—$(CH_2)_q$—;

T is O or S;
o is a number 0 or 1;
p,q are identical or different and are a number from 0–2;
$R^{15}$ is 1. hydrogen
2. $(C_1-C_5)$-alkyl,
3. phenyl,
4. $(C_5-C_9)$-heteroaryl, where 3. and 4. can optionally be substituted by one, two or three groups, such as halogen, $NO_2$, $(C_1-C_3)$-alkyl, $(C_1-C_3)$-alkyl, in which the hydrogen atoms are partially or completely replaced by halogen, $(C_1-C_3)$-alkoxy, $(C_1-C_3)$-alkylthio, $NR^{20}R^{21}$, $NR^{20}CO$—$(C_1-C_5)$-alkyl and $NR^{20}CO$-pyridyl $R^{16}$ is hydrogen, $(C_1-C_4)$-alkyl, phenyl;
$R^{17}$ is hydrogen, halogen, $(C_1-C_4)$-alkyl, $NO_2$, $NH_2$;
$R^{20}$ is hydrogen, $(C_1-C_4)$-alkyl, benzyl;
$R^{21}$ is hydrogen, $C(O)$—O—$(C_1-C_5)$-alkyl;
Z is —$R^{14}$—N—$R^{22}$
$R^{22}$ is

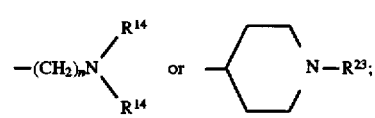

$R^{23}$ is $(C_1-C_4)$-alkyl,

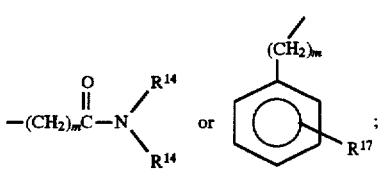

and their physiologically tolerable salts.

Particularly suitable compounds of the formula (I) are also those in which the symbols have the following meaning:

D is a radical of the formula (X)

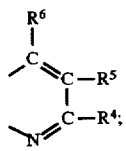

E is a radical of the formula (XI)

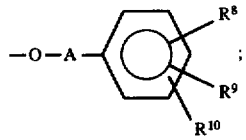

$R^1, R^2$ are identical or different and are hydrogen, halogen or $(C_1-C_4)$-alkyl;
$R^4$ is hydrogen, $(C_1-C_4)$-alkyl;
$R^5$ is hydrogen;
$R^6$ is hydrogen;
$R^8, R^9$ are identical or different and are hydrogen or chlorine;
A is —$CH_2$— or —$CH_2$—$CH_2$—;
$R^{10}$ is a radical of the formula (IX):

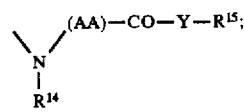

$R^{14}$ is hydrogen, methyl or ethyl;
AA is the amino acid glycine;
Y is
1. $(C_2-C_5)$-alkenediyl,
2. $(C_2-C_4)$-alkanediyl,
3. —$(CH_2)_p$—$T_o$—$(CH_2)_q$—;
T is O or S;
o is a number 0 or 1;
p,q are identical or different and are a number from 0–2;
$R^{15}$ is
1. hydrogen
2. $(C_1-C_3)$-alkyl,
3. phenyl,
4. $(C_5-C_9)$-heteroaryl, where 3. and 4. can optionally be substituted by one, two or three groups, such as halogen, $NO_2$, $(C_1-C_3)$-alkyl, $(C_1-C_3)$-alkyl, in which the hydrogen atoms are partially or completely replaced by halogen, $(C_1-C_3)$-alkoxy, $NR^{20}OR^{21}$, $NR^{20}CO$—$(C_1-C_3)$-alkyl or $NR^{20}CO$-pyridyl;
$R^{20}$ is hydrogen, $(C_1-C_4)$-alkyl, benzyl;
$R^{21}$ is hydrogen, C(O)—O—$(C_1-C_5)$-alkyl; and their physiologically tolerable salts.

Suitable compounds are also

1) N-[1-[4-(1,1-dimethylethyl)phenyl]methylpiperidin-4-yl]-8-methoxy-4-[[4-[[[1-(phenylmethyl)piperidin-4-yl]amino]carbonyl]phenyl]amino]-3-quinolinecarboxamide;
2) N-[1-[(3-chlorophenyl)methyl]piperidin-4-yl]-8-methoxy-4-[[4-[[[1-(phenylmethyl)piperidin-4-yl]amino]carbonyl]phenyl]amino]-3-quinolinecarboxamide;
3) 8-methoxy-N-[1-(phenylmethyl)piperidin-4-yl]-4-[[4-[[[1-(phenylmethyl)piperidin-4-yl]amino]carbonyl]phenyl]amino]-3-quinolinecarboxamide;
4) N-[2-(dimethylamino)ethyl]-8-methoxy-4-[[4-[[[1-(phenylmethyl)piperidin-4-yl]amino]carbonyl]phenyl]amino]-3-quinolinecarboxamide trifluoroacetate;
5) N-[2-(dimethylamino)ethyl]-N-ethyl-8-methoxy-4-[[4-[[[1-(phenylmethyl)piperidin-4-yl]amino]carbonyl]phenyl]amino]-3-quinolinecarboxamide;
6) 4-[[4-[[(3-cyclopentyl-1-oxopropyl)-[1-[6-(diethylamino)-6-oxo]-hexylpiperidin-4-yl]amino]methyl]phenyl]amino]-8-methoxy-N-[1-(phenylmethyl)piperidin-4-yl]-3-quinolinecarboxamide;
7) 4-[[4-[[(1-butylpiperidin-4-ylamino]methyl]phenyl]amino]-8-methoxy-N-[1-(phenylmethyl)piperidin-4-yl]-3-quinolinecarboxamide;
8) N-(1-butylpiperidin-4-yl)-8-methoxy-[[4-[[[1-(phenylmethyl)piperidin-4-yl]amino]carbonyl]phenyl]amino]-3-quinolinecarboxamide;
9) N-[1-[6-(diethylamino)-6-oxo]hexylpiperidin-4-yl]-8-methoxy-4-[[4-[[[1-(phenylmethyl)piperidin-4-yl]amino]carbonyl]phenyl]amino]-3-quinolinecarboxamide;
10) 4-[[4-[[(1-butylpiperidin-4-yl)-(1-oxobutyl)amino]methyl]phenyl]amino]-[8-methoxy-N-[1-(phenylmethyl)piperidin-4-yl]]-3-quinolinecarboxamide;
11) N-[1-[4-(diethylamino)carbonyl]phenyl]piperidin-4-yl]-8-methoxy-4-[[4-[[[1-(phenylmethyl)piperidin-4-yl]amino]carbonyl]phenyl]amino]-3-quinolinecarboxamide;
12) N-[1-(2-phenylethyl)piperidin-4-yl]-8-methoxy-4-[[4-[[[1-(phenylmethyl)-piperidin-4-yl]amino]carbonyl]phenyl]amino]-3-quinolinecarboxamide;
13) 4-[[4-[[(1-butylpiperidin-4-yl)amino]carbonyl]phenyl]amino]-8-methoxy-N-[1-(phenylmethyl)piperidin-4-yl]-3-quinolinecarboxamide;
14) 8-methoxy-N-(1-methylpiperidin-4-yl)-4-[[4-[[[1-(phenylmethyl)piperidin-4-yl]amino]carbonyl]phenyl]amino]-3-quinolinecarboxamide;
15) N-[1-(3-methoxyphenyl)-methyl]piperidin-4-yl-8-methoxy-4-[[4-[[[1-(phenylmethyl)piperidin-4-yl]amino]carbonyl]phenyl]amino]-3-quinolinecarboxamide;
16) 8-methoxy-4-[[4-[[[1-(phenylmethyl)piperidin-4-yl]amino]carbonyl]phenyl]-amino]-1-[[3-(trifluoromethyl)phenyl]methylpiperidin-4-yl]-3-quinolinecarboxamide; or
17) 7-chloro-N-[1-(phenylmethyl)piperidin-4-yl]-4-[[4-[[[1-(phenylmethyl)-piperidin-4-yl]amino]carbonyl]phenyl]amino]-3-quinolinecarboxamide;

and their physiologically tolerable salts.

The following compounds of Examples 1–45, listed in Tables 1–3, are also very particularly suitable.

TABLE 1

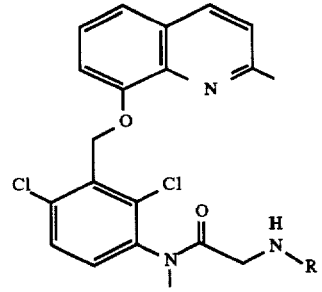

| Example | R |
|---------|---|
| 1 |  |

TABLE 1-continued
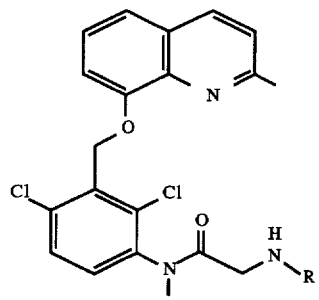
| Example | R |
|---|---|
| 2 | (cinnamaldehyde with 4-(pyridine-2-carboxamido)phenyl) |
| 3 | (cinnamaldehyde with 6-acetamidopyridin-3-yl) |
| 4 | (2,4-hexadienal) |
| 5 | (pentanal) |
| 6 | (cinnamaldehyde) |
TABLE 1-continued
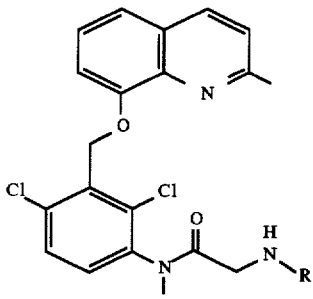
| Example | R |
|---|---|
| 7 | (4-trifluoromethylcinnamaldehyde) |
| 8 | (4-methoxycinnamaldehyde) |
| 9 | (3-methoxycinnamaldehyde) |
| 10 | (3-(2-furyl)acrolein) |
| 11 | (4-dimethylaminocinnamaldehyde) |
| 12 | (2,4-hexadienal) |

TABLE 1-continued
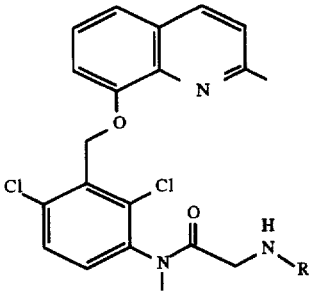
| Example | R |
|---|---|
| 13 | 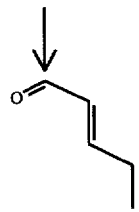 |
| 14 | 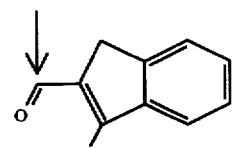 |
| 15 | 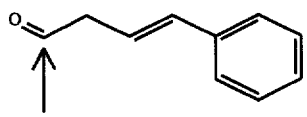 |
| 16 | 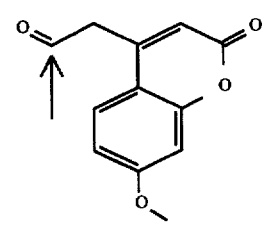 |
| 17 | 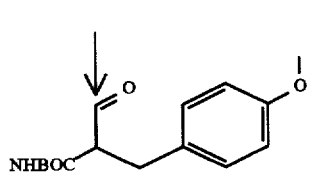 |
| 18 | 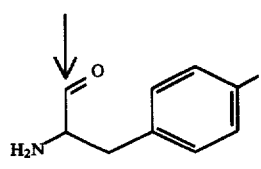 |
| 19 | 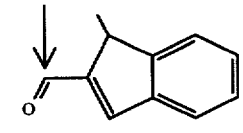 |
TABLE 1-continued
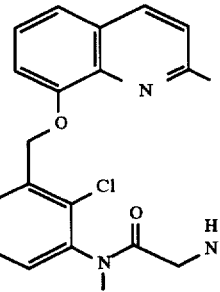
| Example | R |
|---|---|
| 20 | 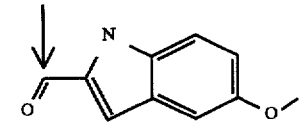 |
| 21 | 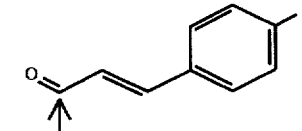 |
| 22 | 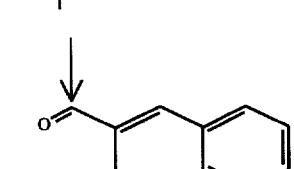 |
| 23 | 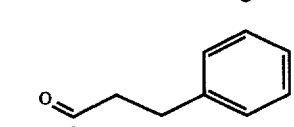 |
| 24 | 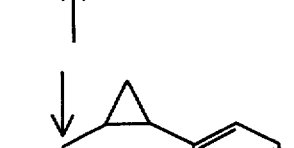 |
| 25 | 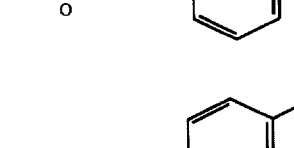 |
| 26 | 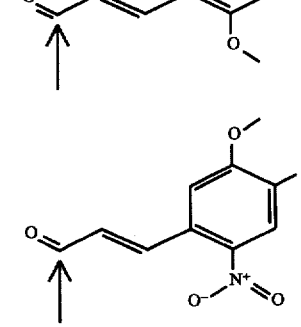 |

TABLE 1-continued

[Structure: 8-((2,4-dichloro-3-(N-methyl-N-(glycyl-NHR))phenyl)methoxy)-2-methylquinoline]

| Example | R |
|---|---|
| 27 | 2,4,5-trimethoxycinnamaldehyde group |
| 28 | 2,3-dimethoxycinnamaldehyde group |
| 29 | phenylthioacetaldehyde group |
| 30 | phenoxyacetaldehyde group |
| 31 | (2,4-dichloro-5-methylphenylthio)acetaldehyde group |
| 32 | (4-methoxyphenoxy)acetaldehyde group |
| 33 | (3-methoxyphenoxy)acetaldehyde group |
| 34 | (4-fluorophenoxy)acetaldehyde group |

TABLE 2

[Structure: methyl-substituted 8-((2,4-dichloro-3-(N-methyl-N-(glycyl-NH-CH=CH-C(O)-R))phenyl)methoxy)-2-methylquinoline]

| Example | R | Pos-CH$_3$ |
|---|---|---|
| 35 | 3-methoxyphenyl | 6 |
| 36 | 3-methoxyphenyl | 5 |
| 37 | 4-methylphenyl | 5 |

TABLE 2-continued

[Structure: quinoline with H₃C substituent, connected via O-CH₂ to dichlorobenzene with N(CH₃)-C(=O)-CH₂-NH-C(=O)-CH=CH-R]

| Example | R | Pos-CH₃ |
|---|---|---|
| 38 | phenyl | 6 |
| 39 | 4-CF₃-phenyl | 5 |
| 40 | 4-CF₃-phenyl | 6 |

TABLE 3

[Structure: quinoline connected via O-CH₂ to dichlorobenzene with N(CH₃)-C(=O)-CH₂-NH-C(=O)-R]

| Example | R |
|---|---|
| 41 | -O-CH₂-C₆H₄-CH₂-NH₂ |
| 42 | -O-CH₂-CH=CH₂ |
| 43 | -O-CH₂-phenyl |
| 44 | -N(allyl) |
| 45 | -N-geranyl |

Administration can be carried out enterally, parenterally—such as, for example, subcutaneously, i.m. or i.v., nasally, rectally or by inhalation. The dose of the active compound depends on the body weight, age and on the manner of administration.

The pharmaceutical preparations of the present invention are prepared in dissolving, mixing, granulating, tableting or sugar-coating processes known per se. For parenteral administration, the active compounds or their physiologically tolerable salts are brought into solution, suspension or emulsion, if desired with the pharmaceutically customary auxiliaries, for example for isotonicization or pH adjustment, and solubilizers, emulsifiers or other auxiliaries.

For the pharmaceuticals described, the use of injectable delayed-release preparations for subcutaneous or intramuscular administration is also useful. Pharmaceutical forms which can be used are, for example, oily crystal suspensions, microcapsules, microparticles, nanoparticles or implants, it being possible to construct the latter from tissue-compatible polymers, in particular biodegradable polymers, such as, for example, on the basis of polylactic acid-polyglycolic acid copolymers. Other conceivable polymers are polyamides, polyesters, polyacetates or polysaccharides.

For the oral administration form, the active compounds are mixed with the additives customary for this purpose such as excipients, stabilizers or inert diluents and brought by means of customary methods into suitable administration forms, such as tablets, coated tablets, hard gelatin capsules, aqueous, alcoholic or oily suspensions or aqueous, alcoholic or oily solutions. Inert excipients which can be used are, for example, gum arabic, magnesia, magnesium carbonate, potassium phosphate, lactose, glucose, magnesium stearylfumarate or starch, in particular corn starch. In this case, preparation of solid pharmaceutical forms can take place either as dry or moist granules. Suitable oily excipients or solvents are, for example, vegetable or animal oils, such as sunflower oil and cod-liver oil.

Oral delayed-release preparations or preparations having enteric coatings are also conceivable. Delayed-release preparations can be constructed on the basis of fat, wax or polymer embeddings. In this context, multilayer or coated tablets or pellets are also suitable.

For the pharmaceuticals described, administration to mucous membranes to achieve systemically active levels is also useful. This relates to the possibility of administration intranasally, by inhalation and rectally.

For the intranasal administration form, the compounds are mixed with the additives customary for this purpose such as stabilizers or inert diluents and brought by means of customary methods into suitable administration forms, such as powders, aqueous, alcoholic or oily suspensions or aqueous, alcoholic or oily solutions. Chelating agents, such as ethylenediamine-N,N,N',N'-tetraacetic acid and buffers such as acetic acid, phosphoric acid, citric acid, tartaric acid and their salts can be added to aqueous intranasal preparations. Multiple dose containers contain preservatives such as benzalkonium chloride, chlorobutanol, chlorhexidine, sorbic acid, benzoic acid, PHB esters or organomercury compounds.

The administration of the nasal solutions can be carried out by means of metered atomizers or as nasal drops having a viscosity-enhancing component, or nasal gels or nasal creams. For administration by inhalation, atomizers or pressurized gas packs using inert carrier gases can be used.

For administration of powders for nasal or pulmonary inhalation, special applicators are necessary.

The active dose of the compounds of the formula (I) is at least 0.01 mg/kg/day, preferably at least 0.1 mg/kg/day, at most 30 mg/kg/day, preferably 0.3 to 10 mg/kg/day of body weight, depending on the severity of the symptoms, based on an adult of 75 kg body weight.

The term "Patient" means a mammal such as a dog, cat, guinea pig, mouse, rat or human being.

The terms "Treating" or "to treat" means to alleviate symptoms, eliminate the causation either on a temporary or permanent basis, or to prevent or slow the appearance of symptoms of chronic fibrogenetic liver disorders (hepatic cirrhosis and hepatic fibrosis) and acute liver disorders.

An effective amount of a compound of formula (I) refers to an amount which is effective, upon single or multiple dose administration to the patient, in treating the chronic fibrogenetic liver disorders (hepatic cirrhosis and hepatic fibrosis) and acute liver disorders or in prolonging the survivability of the patient beyond that expected in the absence of such treatment.

The present invention provides a method of treating a patient suffering from chronic fibrogenetic liver disorders (hepatic cirrhosis and hepatic fibrosis) and acute liver disorders and for the prevention of complications comprising administering to said patient an effective amount of a nonpeptide bradykinin antagonists or their physiologically tolerable salts, such as a compound of formula (I).

Test:

Action of the compound from Example 6 (=compound A) on urine and electrolyte excretion in rats with carbon tetrachloride-induced hepatic fibrosis.

1) Method

Hepatic fibrosis was induced in Wistar rats (breeder: Hoechst AG, Kastengrund) with an initial body weight of 120–150 g, as described by Bickel et al. (J. Hepatol. 1991; 13 (Suppl. 3), pp 26–33). To do this, the animals received carbon tetrachloride ($CCl_4$) twice weekly in a dose of 1 ml/kg orally for at least 6 weeks. The fibrosis of the liver was verified by means of the collagen content of the liver and liver-relevant serum parameters (bilirubin, ALAT, bile acids).

In the course of the fibrogenesis, the animals were kept under standard conditions as follows: day/night rhythm (light phase from 6.30 to 18.30), room temperature 22°±2° C. and relative atmospheric humidity 60±10%. The animals received standardized rat feed (Altromin® 1321) and water ad libitum.

2) Saluresis and diuresis test:

At the time of the diuresis test, the animals had reached a weight of between 210 and 260 g. Food had already been withdrawn from the animals 16 h before the test and withheld during the entire test. The animals were additionally permitted free access to water up to the actual start of the test.

For the duration of the diuresis test, the animals were kept in special diuresis cages. Controlled diuresis was induced with an oral dose of 20 ml of water per kg of body weight at time 0 h. The excretion of electrolytes and urine volumes were determined separately for each animal in the collection periods from 0–5 and 6–24 h.

Seven days later, the test was carried out again on the same animals with administration of bradykinin antagonists. At time 0 h and 6 h, the animals received 3 mg/kg of body weight of compound A intraperitoneally, dissolved in 5 ml/kg of body weight of solution having the following composition: DSMO 28%, ethanol 20%, double-distilled water 44% and 0.9% strength saline solution 8%, pH 5.71.

Sodium and potassium were determined by flame photometry (Eppendorf flame photometer, Hamburg). Chloride was measured argentometrically by means of potentiometric end-point determination (Eppendorf chloride meter, Hamburg). The analytical results were used to calculate the urine excretion (ml/kg of body weight) and electrolyte excretion (mmol/kg of body weight).

3) Result:

Action of compound A on urine and electrolyte excretion in rats with carbon tetrachloride-induced hepatic fibrosis.

TABLE (mean values (MV) ± standard deviation (SD), n = 8)

|  |  | Collection period 1–5h | | Collection period 6–24h | |
| --- | --- | --- | --- | --- | --- |
|  |  | Control | Compound A | Control | Compound A |
| Urine volume | MV | 24.2 | 24.5 | 15.8 | 37.5** |
| (ml/kg) | SD | 3.71 | 11.7 | 6.38 | 9.6 |
| Sodium | MV | 0.329 | 0.92 | 2.03 | 3.45* |
| (mmol/kg) | SD | 0.256 | 1.05 | 0.468 | 1.98 |
| Potassium | MV | 0.868 | 0.839 | 2.37 | 2.58 |
| (mmol/kg) | SD | 0.326 | 0.359 | 1.12 | 0.49 |
| Chloride | MV | 0.375 | 0.704 | 1.78 | 2.77* |
| (mmol/kg) | SD | 0.167 | 0.647 | 0.339 | 1.71 |
| Osmolality | MV | 7.07 | 20.3* | 26.3 | 60.8** |
| (mosmol/kg) | SD | 2.2 | 5.32 | 6.24 | 7.68 |

*$p < 0.05$;
**$p < 0.001$
Dose 3 mg/kg intraperitoneally at time 0 h and 6 h.

4) Statistics:

The results are indicated as arithmetic means and standard deviation (SD). Statistical checking was carried out by the nonparametric Mann-Whitney test.

5) Assessment:

Rats with hepatic fibrosis show a marked increase in diuresis and saluresis after treatment with nonpeptide bradykinin antagonists. As an example, experimental data with the Example compound 6 (compound A) are shown in the above table. A marked, statistically significant increase in diuresis and excretion of sodium and chloride results.

The model of carbon tetrachloride-induced hepatic fibrosis in the rat is generally recognized as a model of hepatic cirrhosis in humans. Overshooting sodium retention is characteristic of hepatic fibrosis and hepatic cirrhosis in humans and animals and is considered to be a consequence of a deep-seated hemodynamic disorder (Schrier et al., Hepatology 1988; 1151–1157). This hemodynamic disorder consists in a portal hypertension, closely coupled with an overshooting peripheral vasodilation, especially in the visceral nervous system (hyperdynamic circulatory situation). The cause of the peripheral vasodilation was unclear until now. The pathological sodium and water retention for its part worsens the symptomatology by contributing, for example, to edema formation and ascites. The portal hypertension is associated with inadequate peripheral vasodilation and sodium retention. These are held responsible for decompensation symptoms in hepatic fibrosis and hepatic cirrhosis. These decompensation symptoms not only include symptoms such as edema formation and ascites, but also the so-called hepatorenal syndrome (kidney failure as a result of a severe liver disorder).

The strong natriuretic action of nonpeptide bradykinin antagonists of the formula (I) in rats with hepatic fibrosis and hepatic cirrhosis is unexpected, because bradykinin antagonists do not show this action in healthy animals and, in contrast, in particular hypertension models can even lead to a decrease in diuresis and sodium excretion (Madeddu et al., Br. J. Pharmacol. 1992; 106: 380–86; Majima et al., Hypertension 1993; 22, 705–714). Bradykinin, for example, can stimulate saluresis and diuresis in the kidney by means of vascular and tubular mechanisms.

Bradykinin is an endogenous peptide having strongly vasodilating and vascular permeability-increasing properties in various vascular regions. Our results show that bradykinin is an essential mediator of excessive sodium retention. An improved hemodynamic and microvascular situation by far overcompensates a possible restriction of the sodium and water excretion by inhibiting the stimulating action of endogenous bradykinin in the kidney such that a therapeutic benefit results. Nonpeptide bradykinin antagonists of the formula (I) are thus suitable for therapeutic and preventive treatment in chronic fibrogenetic liver disorders (hepatic cirrhosis and hepatic fibrosis) and acute liver disorders.

What is claimed is:

1. A method of treating a patient suffering from chronic fibrogenetic liver disorders (hepatic cirrhosis and hepatic fibrosis) and acute liver disorders and for the prevention of complications, comprising, administering to said patient an effective amount of a nonpeptide bradykinin antagonist or a physiologically tolerable salt thereof.

2. The method according to claim 1 wherein the nonpeptide bradykinin antagonist is of the formula (I)

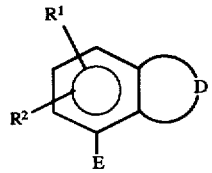 (I)

in which the symbols have the following meaning:
D is
1. a radical of the formula (II):

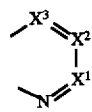 (II)

2. a radical of the formulae (III) to (VI):

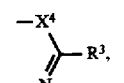 (III)

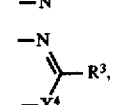 (IV)

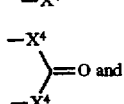 (V)

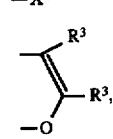 (VI)

E is
1. a radical of the formula (VII):

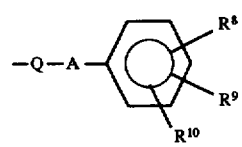 (VII)

2. hydrogen, halogen, $(C_1-C_4)$-alkyl, $(C_1-C_4)$-alkylthio, $(C_1-C_4)$-alkoxy, where in the last 3 radicals 1 or more hydrogen atoms can be replaced by fluorine;
$X^1$ is nitrogen or C—$R^4$;

$X^2$ is nitrogen or C—$R^5$;
$X^3$ is nitrogen or C—$R^6$;
$X^4$ is oxygen, nitrogen or N—$R^7$;
$R^1, R^2$ are identical or different and are hydrogen, halogen, $(C_1-C_4)$-alkyl or $(C_1-C_4)$-alkoxy;
$R^3$ is hydrogen, halogen, $(C_1-C_6)$-alkyl, $(C_6-C_{12})$-aryl, $(C_1-C_3)$-alkyl-$(C_6-C_{12})$-aryl, $(C_3-C_5)$-alkenyl, $(C_1-C_4)$-alkoxy, $CO_2R^{11}$;
$R^4$ is hydrogen, halogen, $(C_1-C_4)$-alkyl, hydroxyl, $(C_1-C_4)$-alkylthio, amino, $(C_1-C_4)$-alkylamino, $(C_1-C_4)$-dialkylamino, $(C_1-C_4)$-alkoxy, which is optionally substituted by hydroxyl, $(C_1-C_4)$-alkoxy, amino or $(C_1-C_4)$-alkylamino, and $(C_6-C_{12})$-aryl, optionally substituted by $(C_1-C_4)$-alkyl or $CO_2R^{11}$;
$R^5$ is
1. hydrogen or $(C_1-C_4)$-alkyl
2. 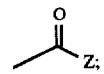

$R^6$ is
1. hydrogen, halogen, $(C_1-C_4)$-alkyl, hydroxyl, $(C_1-C_4)$-alkylthio, amino, $(C_1-C_4)$-alkylamino, $(C_1-C_4)$-dialkylamino, $(C_1-C_4)$-alkoxy, which is optionally substituted by hydroxyl, $(C_1-C_4)$-alkoxy, amino or $(C_1-C_4)$-alkylamino, and $(C_6-C_{12})$-aryl, optionally substituted by $(C_1-C_4)$-alkyl or $CO_2R^{11}$;
2. a radical of the formula (VIII):

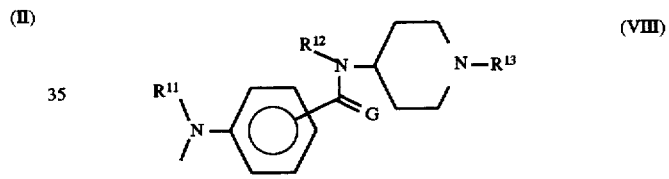 (VIII)

$R^7$ is $(C_1-C_4)$-alkyl, $(C_6-C_{12})$-aryl, or $(C_1-C_3)$-alkyl-$(C_6-C_{12})$-aryl;
$R^8, R^9$ are identical or different and are hydrogen or halogen;
A is $(C_1-C_3)$-alkanediyl;
Q is O or $NR^{11}$;
$R^{10}$ is a radical of the formula (IX)

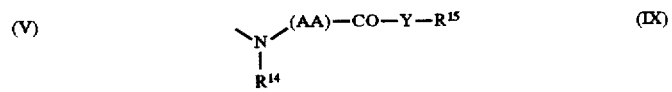 (IX)

$R^{11}, R^{14}$ are hydrogen or $(C_1-C_4)$-alkyl;
G is O or $H_2$;
$R^{12}$ is hydrogen if G=O and hydrogen or $R^{16}CO$ if G=$H_2$;
$R^{13}$ is $(C_1-C_4)$-alkyl, $(C_3-C_7)$-cycloalkyl, —$(CH_2)_m$—$(C_3-C_7)$-cycloalkyl, —$(CH_2)_m$—$CONR^{11}R^{11}$, or

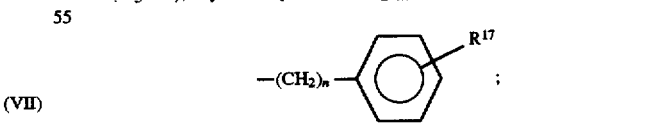

m, n are identically or differently a number 0–6;
AA is an amino acid comprising, methionine, alanine, phenylalanine, 2-chlorophenylalanine, 3-chlorophenylalanine, 4-chlorophenylalanine, 2-fluorophenylalanine, 3-fluorophenylalanine, 4-fluorophenylalanine, tyrosine, o-methyltyrosine, β-(2-thienyl)-alanine, glycine, cyclohexylalanine, leucine, isoleucine, valine, norleucine, phenylglycine, serine, cysteine, aminopropionic acid or aminobutyric acid;

Y is
1. $(C_2-C_6)$-alkenediyl,
2. $(C_1-C_8)$-alkanediyl,
3. $(C_3-C_{10})$-cycloalkenediyl,
4. $-(CH)_p-T_o-(CH_2)_q-$, where 1. to 4. can optionally be substituted by one or more radicals such as, for example, $O-R^{18}$, $NO_2$, $CN$, $CO_2R^{11}$, $SO_3R^{18}$, $NR^{20}R^{21}$, $SO_2NR^{20}R^{21}$, $CONR^{20}R^{21}$;

T is O, $NR^{21}$ or S;
o is a number 0 or 1;
p,q are identical or different and are a number from 0 to 6;
$R^{15}$ is
1. hydrogen,
2. $(C_1-C_5)$-alkyl,
3. $(C_6-C_{10})$-aryl,
4. $(C_1-C_9)$-heteroaryl, where 3. and 4. can optionally be substituted by one or more groups, such as halogen, CN, $NO_2$, $(C_1-C_6)$-alkyl, $(C_6-C_{10})$-aryl, $(C_2-C_5)$-alkenyl, where the last three radicals can optionally be partially or completely substituted by halogen, $(C_1-C_5)$-alkoxy; $(C_1-C_5)$-alkylthio, $NR^{20}R^{21}$, $CO_2R^{19}$, $SO_3R^{18}$, $SO_2NR^{20}R^{21}$, $SO_2R^{18}$, $O-R^{18}$; $NR^{20}CO-R^{15}$;

$R^{16}$ is hydrogen, $(C_1-C_4)$-alkyl, $(C_6-C_{12})$-aryl, $(C_1-C_4)$-alkyl-$(C_6-C_{12})$-aryl, perfluoro-$(C_1-C_4)$-alkyl;

$R^{17}$ is hydrogen, halogen, $(C_1-C_4)$-alkyl, $(C_1-C_4)$-alkoxy, perfluoro-$(C_1-C_4)$-alkyl, $NO_2$, $OH$, $NH_2$, $CONR^{16}R^{16}$, $NR^{16}CONR^{16}R^{16}$;

$R^{18}$, $R^{19}$, $R^{20}$ are identical or different and are hydrogen, $(C_1-C_5)$-alkyl, $(C_3-C_5)$-alkenyl, $(C_6-C_{12})$-aryl-$(C_1-C_3)$-alkyl, $(C_3-C_{10})$-cycloalkyl, $(C_3-C_{10})$-cycloalkyl-$(C_1-C_3)$-alkyl, $C(O)-O-(C_1-C_5)$-alkyl, or $C(O)-NH-(C_1-C_5)$-alkyl;

$R^{21}$ is hydrogen, $C(O)-O-(C_1-C_5)$-alkyl, $C(O)-O-(C_1-C_3)$-alkyl-$(C_6-C_{10})$-aryl;

Z is $-R^{14}N-R^{22}$;
$R^{22}$ is

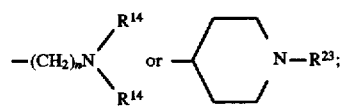

$R^{23}$ is $(C_1-C_4)$-alkyl,

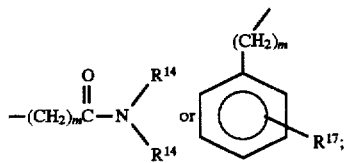

or its physiologically tolerable salts.

3. The method according to claim 2 wherein;
D is a radical of the formula (X)

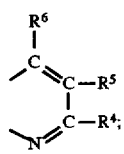 (X)

E is 1. a radical of the formula (XI)

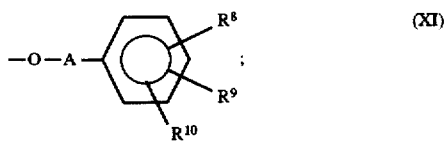 (XI)

2. hydrogen, $(C_1-C_4)$-alkyl or $(C_1-C_4)$-alkoxy;
$R^1,R^2$ are identical or different and are hydrogen, halogen or $(C_1-C_4)$-alkyl;
$R^4$ is hydrogen, $(C_1-C_4)$-alkyl, phenyl or methoxy;
$R^5$ is
1. hydrogen or $(C_1-C_4)$-alkyl;

2. 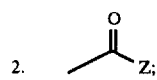

$R^6$ is
1. hydrogen or $(C_1-C_4)$-alkyl
2. a radical of the formula (VIII):

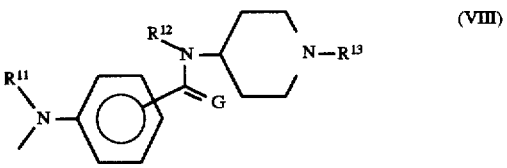 (VIII)

$R^8,R^9$ are identical or different and are hydrogen or chlorine;
A is $-CH_2-$ or $-CH_2-CH_2-$;
$R^{10}$ is a radical of the formula (IX):

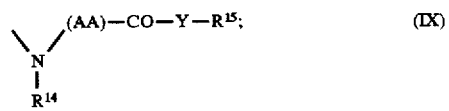 (IX)

$R^{11},R^{14}$ are hydrogen, methyl or ethyl;
G is O or $H_2$;
$R^{12}$ is hydrogen if G is equal to O or hydrogen or $R^{16}CO$ if G is equal to $H_2$;
$R^{13}$ is $(C_1-C_4)$-alkyl, cyclopentyl, cyclohexyl, $-(CH_2)_m CONR^{11}R^{11}$,

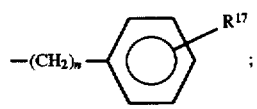

m,n are identically or differently a number 0–2;
AA is the amino acid glycine or alanine;
Y is
1. $(C_2-C_5)$-alkenediyl,
2. $(C_2-C_4)$-alkanediyl,
3. $-(CH_2)_p-T_o-(CH_2)_q-$;

T is O or S;
o is a number 0 or 1;
p,q are identical or different and are a number from 0–2;
$R^{15}$ is
1. hydrogen
2. $(C_1-C_5)$-alkyl,
3. phenyl,
4. $(C_5-C_9)$-heteroaryl, where 3. and 4. can optionally be substituted by one, two or three groups, such as halogen, $NO_2$, $(C_1-C_3)$-alkyl, $(C_1-C_3)$-alkyl, in which the hydrogen atoms are partially or completely replaced by halogen, $(C_1-C_3)$-alkoxy, $(C_1-C_3)$-alkylthio, $NR^{20}R^{21}$, $NR^{20}CO$—$(C_1-C_5)$-alkyl and $NR^{20}CO$-pyridyl $R^{16}$ is hydrogen, $(C_1-C_4)$-alkyl, phenyl;
$R^{17}$ is hydrogen, halogen, $(C_1-C_4)$-alkyl, $NO_2$, $NH_2$;
$R^{20}$ is hydrogen, $(C_1-C_4)$-alkyl, benzyl;
$R^{21}$ is hydrogen, $C(O)$—$O$—$(C_1-C_5)$-alkyl;
Z is —$R^{14}$—N—$R^{22}$
$R^{22}$ is

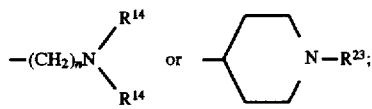

$R^{23}$ is $(C_1-C_4)$-alkyl,

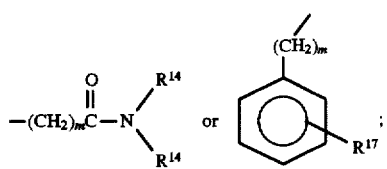

or its physiologically tolerable salts.

4. The method according to either claim 2 or claim 3 wherein:
D is a radical of the formula (X)

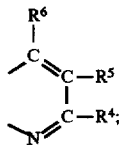

(X)

E is a radical of the formula (XI)

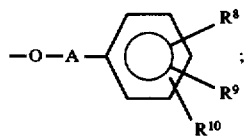

(XI)

$R^1, R^2$ are identical or different and are hydrogen, halogen or $(C_1-C_4)$-alkyl;

$R^4$ is hydrogen, $(C_1-C_4)$-alkyl;
$R^5$ is hydrogen;
$R^6$ is hydrogen;
$R^8, R^9$ are identical or different and are hydrogen or chlorine;
A is —$CH_2$— or —$CH_2$—$CH_2$—;
$R^{10}$ is a radical of the formula (IX):

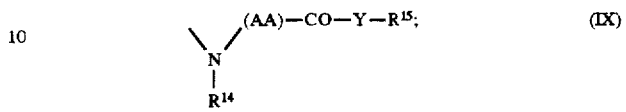

(IX)

$R^{14}$ is hydrogen, methyl or ethyl;
AA is the amino acid glycine;
Y is

1. $(C_2-C_5)$-alkenediyl,
2. $(C_2-C_4)$-alkanediyl,
3. —$(CH_2)_p$—$T_o$—$(CH_2)_q$—;

T is O or S;
o is a number 0 or 1;
p,q are identical or different and are a number from 0–2;
$R^{15}$ is 1. hydrogen
2. $(C_1-C_3)$-alkyl,
3. phenyl,
4. $(C_5-C_9)$-heteroaryl, where 3. and 4. can optionally be substituted by one, two or three groups, such as halogen, $NO_2$, $(C_1-C_3)$-alkyl, $(C_1-C_3)$-alkyl, in which the hydrogen atoms are partially or completely replaced by halogen, $(C_1-C_3)$-alkoxy, $NR^{20}R^{21}$, $NR^{20}$ CO—$(C_1-C_3)$-alkyl or $NR^{20}CO$-pyridyl;

$R^{20}$ is hydrogen, $(C_1-C_4)$-alkyl, benzyl;
$R^{21}$ is hydrogen, $C(O)$—$O$—$(C_1-C_5)$-alkyl;

or its physiologically tolerable salts.

* * * * *

UNITED STATES PATENT AND TRADEMARK OFFICE
CERTIFICATE OF CORRECTION

PATENT NO. : 5,786,365
DATED : July 28, 1998
INVENTOR(S) : HEITSCH et al.

It is certified that error appears in the above-identified patent and that said Letters Patent is hereby corrected as shown below:

On the title page, item[30]:  19620509.3   5/22/96
                              19632042.9   8/8/96
                              19639303.5   9/25/96

Claim 2, column 25, line 57, "its" should read --a--; and "salts" should read --salt thereof--.

Claim 3, column 27, line 26, "its" should read --a--; and "salts" should read --salt thereof--.

Claim 4, column 28, line 42, "its" should read --a--; and "salts" should read --salt thereof--.

Signed and Sealed this

Thirteenth Day of July, 1999

Attest:

Attesting Officer

Q. TODD DICKINSON

Acting Commissioner of Patents and Trademarks